(12) United States Patent
Kim et al.

(10) Patent No.: US 11,744,865 B2
(45) Date of Patent: Sep. 5, 2023

(54) COMPOSITION FOR INHIBITING LIPOFUSCIN ACCUMULATION OR REMOVING LIPOFUSCIN

(71) Applicant: AMOREPACIFIC CORPORATION, Seoul (KR)

(72) Inventors: Eunmi Kim, Yongin-si (KR); Juewon Kim, Yongin-si (KR); Si Young Cho, Yongin-si (KR); Mihee Ji, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 17/726,970

(22) Filed: Apr. 22, 2022

(65) Prior Publication Data

US 2022/0339210 A1  Oct. 27, 2022

(30) Foreign Application Priority Data

Apr. 27, 2021  (KR) .................. 10-2021-0054196

(51) Int. Cl.
*A61K 35/74* (2015.01)
*A23L 33/135* (2016.01)
(Continued)

(52) U.S. Cl.
CPC ............ *A61K 35/74* (2013.01); *A23L 33/135* (2016.08); *A23L 33/40* (2016.08); *A61P 17/00* (2018.01);
(Continued)

(58) Field of Classification Search
CPC ......... A61K 35/74; A61K 8/99; A23L 33/135; A23L 33/40; A61P 17/00; A61P 21/00;
(Continued)

(56) References Cited

U.S. PATENT DOCUMENTS 9,675,650 B2   6/2017  Park et al.
2015/0150785 A1  6/2015  Fisas Verges
(Continued)

FOREIGN PATENT DOCUMENTS

EP    3 190 099 B1   10/2020
JP    2012-41355 A    3/2012
(Continued)

OTHER PUBLICATIONS

Kwon et al., Dairy Propionibacterium extends the mean lifespan of Caenorhabditis elegans via activation of the innate immune system, Sci Reports, 6:31713, DOI: 10.1038/srep31713. Published Aug. 17, 2016 (Year: 2016).*

(Continued)

*Primary Examiner* — Louise W Humphrey
*Assistant Examiner* — Alexander M Duryee
(74) *Attorney, Agent, or Firm* — Sughrue Mion, PLLC

(57) ABSTRACT

A composition for inhibiting lipofuscin accumulation or removing lipofuscin is disclosed. A *Chryseobacterium* sp. strain, a lysate of the *Chryseobacterium* sp. strain, a culture of the *Chryseobacterium* sp. strain, or an extract of the lysate or culture is included in the composition. The composition provides an anti-aging effect by inhibiting lipofuscin accumulation or removing lipofuscin. The composition also provides an effect of preventing, ameliorating or treating the diseases caused by the lipofuscin accumulation, such as skin hyperpigmentation, Alzheimer's disease, Parkinson's disease, amyotrophic lateral sclerosis, myocardial infarction and age-related macular degeneration.

8 Claims, 5 Drawing Sheets

Specification includes a Sequence Listing.

(51) Int. Cl.
*A23L 33/00* (2016.01)
*C12N 1/20* (2006.01)
*A61Q 19/02* (2006.01)
*A61P 17/00* (2006.01)
*A61Q 19/08* (2006.01)
*C12R 1/01* (2006.01)

(52) U.S. Cl.
CPC .............. *A61Q 19/02* (2013.01); *A61Q 19/08* (2013.01); *C12N 1/205* (2021.05); *A23V 2002/00* (2013.01); *C12R 2001/01* (2021.05)

(58) Field of Classification Search
CPC .......... A61P 25/00; A61P 25/28; A61Q 19/02; A61Q 19/08; C12N 1/205; C12N 1/00; A23V 2002/00; C12R 2001/01
See application file for complete search history.

(56) References Cited

U.S. PATENT DOCUMENTS

| | | |
|---|---|---|
| 2016/0095864 A1 | 4/2016 | Park et al. |
| 2016/0113935 A1 | 4/2016 | Jung et al. |
| 2017/0002362 A1 | 1/2017 | Kim et al. |
| 2018/0221444 A1 | 8/2018 | Janson et al. |
| 2019/0192413 A1* | 6/2019 | Kang ............... A61K 8/368 |

FOREIGN PATENT DOCUMENTS

| | | | |
|---|---|---|---|
| JP | 2018-522000 A | | 8/2018 |
| KR | 10-0329962 B1 | | 3/2002 |
| KR | 10-2009-0130837 A | | 12/2009 |
| KR | 10-2011-0106898 A | | 9/2011 |
| KR | 10-1207490 B1 | | 12/2012 |
| KR | 10-2015-0057664 A | | 5/2015 |
| KR | 10-2016-0099163 A | | 8/2016 |
| KR | 10-2018-0035682 A | | 4/2018 |
| KR | 20180035682 A | * | 4/2018 |
| KR | 10-1887631 B1 | | 8/2018 |
| KR | 10-1936687 B1 | | 1/2019 |
| KR | 10-1998210 B1 | | 7/2019 |
| KR | 10-2081204 B1 | | 2/2020 |
| KR | 10-2020-0043283 A | | 4/2020 |
| WO | 99/43350 A1 | | 9/1999 |
| WO | 2010/088225 A2 | | 8/2010 |

OTHER PUBLICATIONS

Dereure, Drug-Induced Skin Pigmentation: Epidemiology, Diagnosis and Treatment, Am J Clin Dermatol 2001; 2 (4): 253-262. (Year: 2001).*
McFarland et al., Strain-Specificity and Disease-Specificity of Probiotic Efficacy: A Systematic Reviewand Meta-Analysis, Front. Med. 5:124., Published May 7, 2018 (Year: 2018).*
Skoczyhska et al., Melanin and lipofuscin as hallmarks of skin aging, Adv Dermatol Allergol 2017; XXXIV (2): 97-103 (Year: 2017).*
Extended European Search Report dated Jun. 22, 2022 in European Application No. 22169746.9.
Database GNPD, "Lifting Toner", Mintel, Database accession No. 9432546, XP055925295, 2022, pp. 1-3 (3 pages total).
Sevda Soydan et al., "Chryseobacterium indolegenes infection in a patient with chronic obstructive pulmonary disease", Drug Discoveries & Therapeutics, 2017, vol. 11, No. 3, pp. 165-167 (3 pages total).
Lipika Singhal et al., "Sepsis Due to Chryseobacterium gleum in a Diabetic Patient with Chronic Obstructive Pulmonary Disease: a Case Report and Mini Review", Japanese Journal of Infectious Diseases, 2017, vol. 70, No. 6, pp. 687-688 (2 pages total).
Anna Skoczyńska et al., "Melanin and lipofuscin as hallmarks of skin aging", Advances in Dermatology and Allergology, 2017, vol. 2, pp. 97-103 (7 pages total).
Erik Edström et al., "Factors contributing to neuromuscular impairment and sarcopenia during aging", Physiology & Behavior, 2007, vol. 92, No. 1-2, pp. 129-135 (7 pages total).
Tatariunas A B et al., "Lipofuscin granule accumulation in the area of an experimental myocardial infarct in young animals", Database Medline, 1980, XP002806736, Database accession No. NLM7406719, vol. 42, No. 8 (1 page total).
Moochang Kook et al., "Chryseobacterium camelliae sp. nov., isolated from green tea", International Journal of Systematic and Evolutionary Microbiology, 2014, vol. 64, pp. 851-857 (7 pages total).

* cited by examiner

[FIG. 1]

AGCTAGGGTGGGTACGGATTATTGGGTTTAAGGGTCCGTAGGCGGATGTGTAAGTCAGTGGTGAAATCTC
ACAGCTTAACTGTGAAACTGCCATTGATACTGCATGTCTTGAGTAAGGTAGAAGTGGCTGGAATAAGTAG
TGTAGCGGTGAAATGCATAGATATTACTTAGAACACCAATTGCGAAGGCAGGTCACTATGTCTTAACTGA
CGCTGATGGACGAAAGCGTGGGGAGCGAACAGGATTAGATACCCTGGTAGTCCACGCCGTAAACGATGCT
AACTCGTTTTTGGGTTTTCGGATTCAGAGACTAAGCGAAAGTGATAAGTTAGCCACCTGGGGAGTACGTT
CGCAAGAATGAAACTCAAAGGAATTGACGGGGGCCCGCACAAGCGGTGGATTATGTGGTTTAATTCGATG
ATACGCGAGGAACCTTACCAAGGCTTAAATGGGAATTGATCGGTTTAGAAATAGACCTTCCTTCGGGCAA
TTTTCAAGGTGCTGCATGGTTGTCGTCAGCTCGTGCCGTGAGGTGTTAGGTTAAGTCCTGCAACGAGCGC
AACCCCTGTTACTAGTTGCTACCATTAAGTTGAGGACTCTAGTAAGACTGCCTACGCAAGTAGAGAGGAA
GGTGGGGATGACGTCAAATCATCACGGCCCTTACGCCTTGGGCCACACACGTAATACAATGGCAGGTACA
GAGGGCAGCTACACAGCGATGTGATGCGAATCTCGAAAGCCTGTCTCAGTTCGGATTGGAGTCTGCAACT
CGACTCTATGAAGCTGGAATCGCTAGTAATCGCGCATCAGCCATGGCGCGGTGAATACGTTCCCGGGCCT
TGTACACACCGCCCGTCAAGCCATGGAAGTCTGGGGTACCTGAAGTCGGTGACCGTAAAAGGAGCTGCCT
AGGGTAAAACAGGTAACTAGGGCTAATCGTACAGGGGAAACCCTAAAAGTTTAACCAGGAACCGGTAGAA
GGTGTTAAGGATAGAGTGTATATCTGTTTGTATATGTTGTATTTATCTAGTGTATCTGAGATAATGGAT
AGATAACGCTCGAACTGGCACTACACTAGTGAGAGATATTAGTATTCTTATATATTAAGTCTCTATTGAG
ATATCATAATCGTGGATAAAGACTTGACAGCGGCGAGAGCCTGGATAGCGGAGTGGTGTTAGCTATGAGT
GTATAATC  (SEQ ID NO: 1)

[FIG. 2]
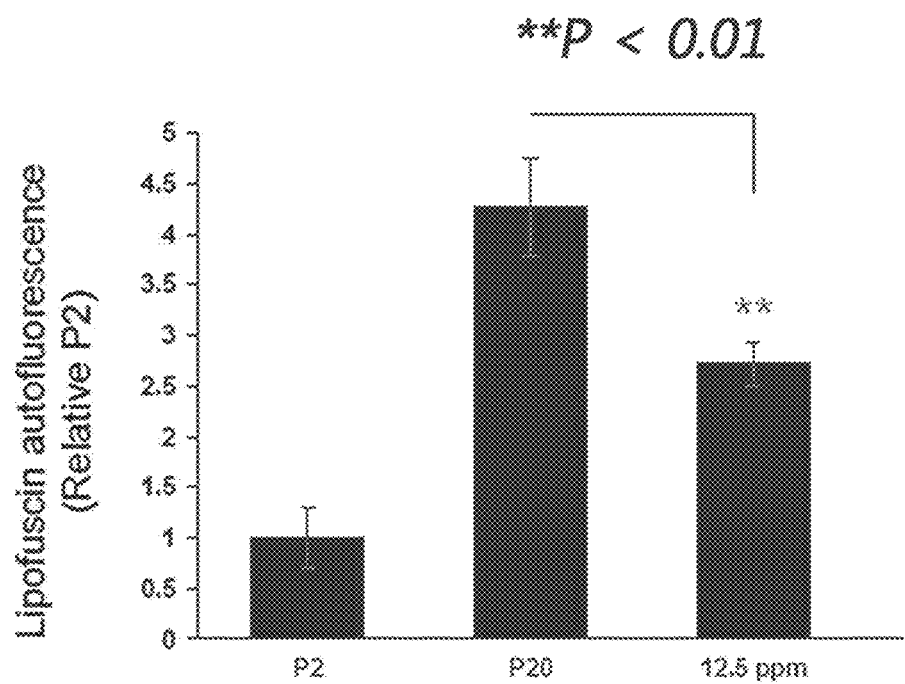

[FIG. 3]
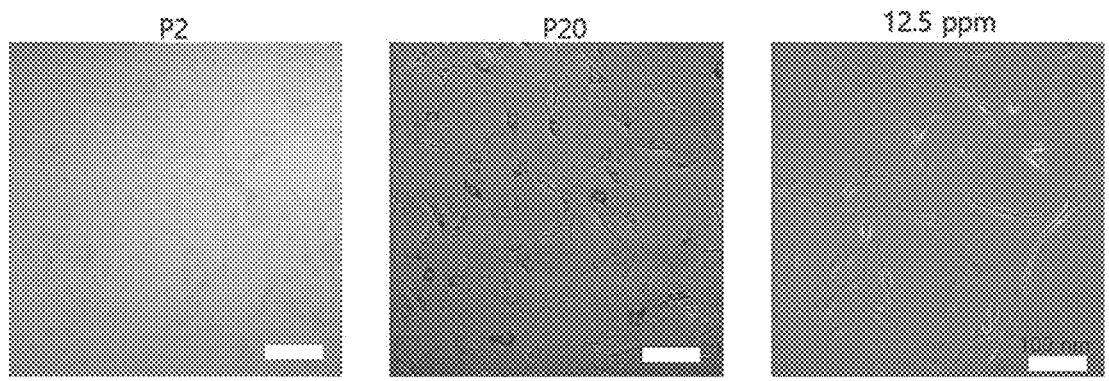

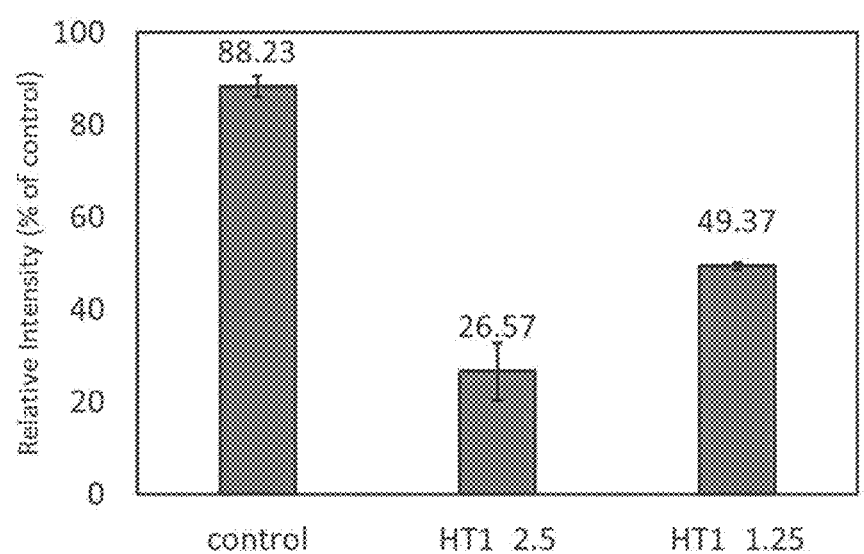
[FIG. 4]

[FIG. 5]
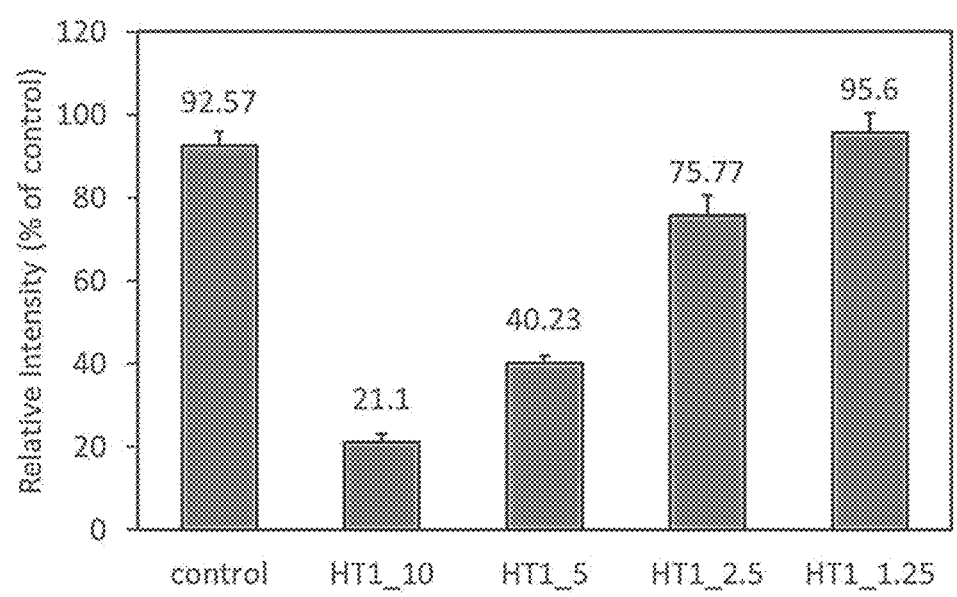

COMPOSITION FOR INHIBITING LIPOFUSCIN ACCUMULATION OR REMOVING LIPOFUSCIN

CROSS-REFERENCE TO RELATION APPLICATION

The present application claims priority to Korean Patent Application No. 10-2021-0054196, filed on Apr. 27, 2021, the entire contents of which are hereby incorporated by reference.

SEQUENCE LISTING

The content of the electronically submitted sequence listing, file name: Sequence_Listing_As_Filed.txt; size: 2,339 bytes; and date of creation: Apr. 21, 2022, filed herewith, is incorporated herein by reference in its entirety.

TECHNICAL FIELD

A composition for inhibiting lipofuscin accumulation or removing lipofuscin is disclosed.

BACKGROUND ART

Lipofuscin is a kind of metabolic wastes produced when various metabolites are digested or processed in intracellular liposomes, and is a yellowish-brown pigmented granule physiologically present in the myocardium. As the amount of lipofuscin accumulates in the cell, the cell function decreases and the aging rate increases.

The heart tissue of a long-lived elderly person is brownish and has a reduced size because of the increase in lipofuscin pigment, which is called brown atrophy of heart. Such pigmentation may also occur in the liver, which is called brown atrophy of liver. In addition, cases of lipofuscin pigmentation in the heart, liver, and kidneys of cancer patients or patients with long-term wasting diseases such as severe pulmonary tuberculosis have been reported. On the other hand, when the skin is aging, the most prominent phenomenon is pigmentation such as melasma and liver spots, and such pigmentation is a phenomenon in which lipofuscin is accumulated. For this reason, lipofuscin is also called 'liver spot in the body'. Therefore, inhibiting the production and/or accumulation of lipofuscin so that lipofuscin does not accumulate in skin cells is very important in preventing skin aging.

As described above, lipofuscin, which is naturally occurring in the metabolic process of cells, is accumulated in cells in a greater amount when cellular functions decline as well as aging or when repeatedly exposed to external toxins. In addition, the accumulated lipofuscin interferes with the normal function of cells and further accelerates the aging rate. Lipofuscin is found not only in skin cells but also in liver, kidney, heart muscle, retina, adrenal gland, nerve cells and ganglion cells, and is known to accumulate in important body organs and cause various degenerative diseases. For example, when lipofuscin accumulates in the heart muscle, it can worsen the heart muscle and cause myocardial infarction, and when lipofuscin accumulates in the retina or nerve cells, it can cause macular degeneration or Alzheimer's disease. In addition, when it accumulates in organs such as the adrenal gland and liver, pituitary gland, which secrete hormones, abnormalities in the metabolic function of body hormones such as growth hormone and sex hormone may occur.

DISCLOSURE

Technical Problem

In one aspect, an object of the present disclosure is to provide a composition for inhibiting lipofuscin accumulation or removing lipofuscin.

Technical Solution

In one aspect, the present disclosure provides a method for inhibiting lipofuscin accumulation or removing lipofuscin, comprising administering to a subject in need thereof a composition comprising a *Chryseobacterium* sp. strain, a lysate of the *Chryseobacterium* sp. strain, a culture of the *Chryseobacterium* sp. strain, or an extract of the lysate or culture in an effective amount.

In an exemplary embodiment, the composition may comprise the culture of the *Chryseobacterium* sp. strain, or the extract of the culture in an effective amount.

In an exemplary embodiment, the strain may be a *Chryseobacterium camelliae* strain.

In an exemplary embodiment, the strain may be a *Chryseobacterium camelliae* Dolsongi-HT1 strain having accession number of KCCM11883P.

In an exemplary embodiment, the subject may be in need of anti-aging.

In an exemplary embodiment, the subject may be in need of anti-aging by inhibiting lipofuscin accumulation or removing lipofuscin.

In an exemplary embodiment, the subject may be in need of skin whitening.

In an exemplary embodiment, the subject may be in need of skin whitening by inhibiting lipofuscin accumulation or removing lipofuscin.

In an exemplary embodiment, the subject may be in need of preventing, ameliorating or treating a disease caused by the lipofuscin accumulation.

In an exemplary embodiment, the disease caused by the lipofuscin accumulation may comprise one or more selected from the group consisting of skin hyperpigmentation, sarcopenia, progeria, Alzheimer's disease, Parkinson's disease, amyotrophic lateral sclerosis (ALS), myocardial infarction, age-related macular degeneration, neuronal ceroid lipofuscinoses (NCL), acromegaly, denervation atrophy and chronic obstructive pulmonary disease (COPD).

In an exemplary embodiment, the skin hyperpigmentation may be one or more selected from the group consisting of melasma, liver spot, freckle, lentigo, nevus, pigmentation caused by drug, and pigmentation caused by inflammation.

In an exemplary embodiment, the composition may be a cosmetic composition, a food composition, or a pharmaceutical composition.

In an exemplary embodiment, the composition may comprise 0.0001 to 99.99% by weight of the *Chryseobacterium* sp. strain, the lysate of the *Chryseobacterium* sp. strain, the culture of the *Chryseobacterium* sp. strain, or the extract of the lysate or culture, based on a total weight of the composition.

Advantageous Effects

In one aspect, the technology disclosed herein has the effect of providing a composition for inhibiting lipofuscin accumulation or removing lipofuscin.

BRIEF DESCRIPTION OF DRAWINGS

FIG. 1 shows the partial 16S rDNA sequence (SEQ ID NO: 1) of a *Chryseobacterium camelliae* Dolsongi-HT1 strain according to one embodiment.

FIG. 2 shows a graph in which a change in an amount of lipofuscin accumulation according to cellular senescence is confirmed in one embodiment.

FIG. 3 shows a fluorescence micrograph in which a change in an amount of lipofuscin accumulation according to cellular senescence is confirmed in one embodiment.

FIG. 4 shows a graph in which the lipofuscin removal efficacy of a culture of *Chryseobacterium* sp. strain in keratinocytes is confirmed in one embodiment.

FIG. 5 shows a graph in which lipofuscin removal efficacy of a culture of *Chryseobacterium* sp. strain in fibroblasts is confirmed in one embodiment.

BEST MODE

Hereinafter, the present disclosure will be described in detail.

In one aspect, the present disclosure provides a composition for inhibiting lipofuscin accumulation or removing lipofuscin, comprising a *Chryseobacterium* sp. strain, a lysate of the *Chryseobacterium* sp. strain, a culture of the *Chryseobacterium* sp. strain, or an extract of the lysate or culture as an active ingredient.

In another aspect, the present disclosure provides a composition for preventing, ameliorating or treating a disease caused by the lipofuscin accumulation, comprising a *Chryseobacterium* sp. strain, a lysate of the *Chryseobacterium* sp. strain, a culture of the *Chryseobacterium* sp. strain, or an extract of the lysate or culture as an active ingredient.

In still another aspect, the present disclosure provides a method for inhibiting lipofuscin accumulation or removing lipofuscin, comprising administering to a subject in need thereof a composition comprising a *Chryseobacterium* sp. strain, a lysate of the *Chryseobacterium* sp. strain, a culture of the *Chryseobacterium* sp. strain, or an extract of the lysate or culture in an effective amount.

In still another aspect, the present disclosure provides a method for preventing, ameliorating or treating a disease caused by lipofuscin accumulation, comprising administering to a subject in need thereof a composition comprising a *Chryseobacterium* sp. strain, a lysate of the *Chryseobacterium* sp. strain, a culture of the *Chryseobacterium* sp. strain, or an extract of the lysate or culture in an effective amount.

In still another aspect, the present disclosure provides a composition comprising a *Chryseobacterium* sp. strain, a lysate of the *Chryseobacterium* sp. strain, a culture of the *Chryseobacterium* sp. strain, or an extract of the lysate or culture for use in inhibition of lipofuscin accumulation or removal of lipofuscin.

In still another aspect, the present disclosure provides a composition comprising a *Chryseobacterium* sp. strain, a lysate of the *Chryseobacterium* sp. strain, a culture of the *Chryseobacterium* sp. strain, or an extract of the lysate or culture for use in the prevention, amelioration or treatment of a disease caused by lipofuscin accumulation.

In still another aspect, the present disclosure provides a use of a composition comprising a *Chryseobacterium* sp. strain, a lysate of the *Chryseobacterium* sp. strain, a culture of the *Chryseobacterium* sp. strain, or an extract of the lysate or culture for inhibition of lipofuscin accumulation or removal of lipofuscin.

In still another aspect, the present disclosure provides a use of a composition comprising a *Chryseobacterium* sp. strain, a lysate of the *Chryseobacterium* sp. strain, a culture of the *Chryseobacterium* sp. strain or an extract of the lysate or culture for the prevention or amelioration of a disease caused by lipofuscin accumulation.

In still another aspect, the present disclosure provides a use of a composition comprising a *Chryseobacterium* sp. strain, a lysate of the *Chryseobacterium* sp. strain, a culture of the *Chryseobacterium* sp. Strain or an extract of the lysate or culture in manufacturing a composition for inhibiting lipofuscin accumulation or removing lipofuscin.

In still another aspect, the present disclosure provides a use of a composition comprising a *Chryseobacterium* sp. strain, a lysate of the *Chryseobacterium* sp. strain, a culture of the *Chryseobacterium* sp. strain, or an extract of the lysate or culture in manufacturing a composition for preventing, ameliorating or treating a disease caused by lipofuscin accumulation.

As used herein, the term "active ingredient" refers to a component capable of exhibiting a desired activity alone or in combination with a carrier having no activity by itself.

The 'lysate' refers to a product obtained by crushing a microorganism itself by chemical or physical force.

The 'culture' refers to some or all substances contained in a medium in which the microorganisms are cultured, regardless of the form of the culture. For example, the culture may include metabolites or secretions resulting from microbial culture. In addition, the microorganism itself may be included in the culture.

In an exemplary embodiment, the culture is a culture solution itself obtained by culturing the microorganism according to the present disclosure in a suitable liquid medium, a filtered solution (filtrate or centrifuged supernatant) obtained by filtering or centrifuging the culture solution to remove microorganisms, a lysate obtained by sonicating the culture solution or treating the culture solution with a lysozyme, or a concentrated powder obtained by concentrating and freeze-drying the culture solution.

In an exemplary embodiment, the culture may be a culture solution.

In an exemplary embodiment, the culture may be a culture solution obtained by culturing the strain in a liquid medium and then removing the strain.

In an exemplary embodiment, the culture may be a concentrate obtained by concentrating the culture solution.

The 'extract' refers to a product obtained by extracting the lysate or the culture regardless of an extraction method, an extraction solvent, an extracted component, or the form of the extract. The extract is the broadest concept including all substances that can be obtained by processing or treating by other methods such as concentration, drying, fractionation, etc. after extraction.

In an exemplary embodiment, the extract may be one extracted with one or more extraction solvents selected from the group consisting of water, anhydrous or hydrous alcohol having 1 to 6 carbon atoms (e.g., methanol, ethanol, propanol or butanol), propylene glycol, butylene glycol, dipropylene glycol, glycerin, acetone, ethyl acetate, chloroform, methylene chloride, butyl acetate, diethyl ether, dichloromethane, hexane, and a mixture thereof.

In an exemplary embodiment, the extract may be extracted with a solvent selected from water, alcohol or a mixture thereof, preferably a $C_1$ to $C_4$ lower alcohol or a mixed solvent thereof, and more specifically, methanol or an aqueous ethanol solution.

In an exemplary embodiment, the composition comprising the *Chryseobacterium* sp. strain, the lysate of the *Chryseobacterium* sp. strain, the culture of the *Chryseobacterium* sp. strain, or an extract of the lysate or the culture may be a composition comprising the culture of the *Chryseobacterium* sp. strain or the extract of the culture as an active ingredient.

In an exemplary embodiment, the composition comprising the *Chryseobacterium* sp. strain, the lysate of the *Chryseobacterium* sp. strain, the culture of the *Chryseobacterium* sp. strain, or the extract of the lysate or the culture may be a composition comprising the culture of the *Chryseobacterium* sp. strain as an active ingredient.

In an exemplary embodiment, the strain may be a *Chryseobacterium camelliae* strain.

In an exemplary embodiment, the strain may be a *Chryseobacterium camelliae* Dolsongi-HT1 strain having accession number of KCCM11883P.

In an exemplary embodiment, the *Chryseobacterium camellia* Dolsongi-HT1 strain may have the partial 16S rDNA sequence of SEQ ID NO: 1.

In an exemplary embodiment, the composition for inhibiting lipofuscin accumulation or removing lipofuscin and/or the composition for preventing, ameliorating or treating a disease caused by lipofuscin accumulation may be an anti-aging composition.

As used herein, the term 'anti-aging use' refers to the use of preventing, delaying and/or ameliorating the aging phenomenon caused by internal factors including genetic factors and external factors including ultraviolet rays. The composition provides an effect of preventing, ameliorating or treating a disease or symptom associated with cellular senescence by reducing the level of cellular senescence.

In an exemplary embodiment, the composition for inhibiting lipofuscin accumulation or removing lipofuscin and/or the composition for preventing, ameliorating or treating a disease caused by lipofuscin accumulation may be a whitening composition.

In an exemplary embodiment, the composition comprising the *Chryseobacterium* sp. strain, the lysate of the *Chryseobacterium* sp. strain, the culture of the *Chryseobacterium* sp. strain, or the extract of the lysate or the culture may be one for preventing, ameliorating or treating the disease caused by lipofuscin accumulation.

In an exemplary embodiment, the disease caused by the lipofuscin accumulation may comprise one or more selected from the group consisting of skin hyperpigmentation, sarcopenia, progeria, Alzheimer's disease, Parkinson's disease, amyotrophic lateral sclerosis (ALS), myocardial infarction, age-related macular degeneration, neuronal ceroid lipofuscinoses (NCL), acromegaly, denervation atrophy and chronic obstructive pulmonary disease (COPD).

In an exemplary embodiment, the skin hyperpigmentation may be one or more selected from the group consisting of melasma, liver spots, freckles, lentigo, nevus, pigmentation caused by drugs, and pigmentation caused by inflammation.

In an exemplary embodiment, the composition comprising the *Chryseobacterium* sp. strain, the lysate of the *Chryseobacterium* sp. strain, the culture of the *Chryseobacterium* sp. strain, or the extract of the lysate or culture can inhibit skin hyperpigmentation to act on whitening and/or skin tone improvement.

In an exemplary embodiment, the composition comprising the *Chryseobacterium* sp. strain, the lysate of the *Chryseobacterium* sp. strain, the culture of the *Chryseobacterium* sp. strain, or the extract of the lysate or culture may be a cosmetic composition, a food composition or a pharmaceutical composition.

In an exemplary embodiment, the composition comprising the *Chryseobacterium* sp. strain, the lysate of the *Chryseobacterium* sp. strain, the culture of the *Chryseobacterium* sp. strain, or the extract of the lysate or culture may be administered or applied to a subject in the form of a cosmetic composition, a food composition or a pharmaceutical composition.

According to an exemplary embodiment, the composition comprising the *Chryseobacterium* sp. strain, the lysate of the *Chryseobacterium* sp. strain, the culture of the *Chryseobacterium* sp. strain, or the extract of the lysate or culture may be a cosmetic composition.

The cosmetic composition may further include functional additives and components included in general cosmetic compositions. The functional additive may include a component selected from the group consisting of water-soluble vitamins, oil-soluble vitamins, high-molecular peptides, high-molecular polysaccharides, sphingolipids, and seaweed extract. As other ingredients included, there may be oil and fat ingredients, moisturizers, emollients, surfactants, organic and inorganic pigments, organic powders, UV absorbers, preservatives, fungicides, antioxidants, plant extracts, pH regulators, alcohols, pigments, fragrances, blood circulation accelerators, cooling agents, anti-perspiration agents, purified water, etc.

The cosmetic composition is not particularly limited in formulation, and may be appropriately selected according to the purpose. For example, the cosmetic composition may be prepared in any one or more formulations selected from the group consisting of skin lotion, skin softener, skin toner, astringent, lotion, milk lotion, moisture lotion, nourishing lotion, massage cream, nourishing cream, moisture cream, hand cream, foundation, essence, nourishing essence, pack, soap, cleansing foam, cleansing lotion, cleansing cream, body lotion and body cleanser, but is not limited thereto.

When the formulation of the composition is a paste, cream or gel, animal fiber, vegetable fiber, wax, paraffin, starch, tracanth, cellulose derivative, polyethylene glycol, silicone, bentonite, silica, talc, zinc oxide and the like may be used as a carrier component.

When the formulation of the composition is a powder or a spray, lactose, talc, silica, aluminum hydroxide, calcium silicate or polyamide powder may be used as a carrier component, and in particular, when the formulation of the composition is a spray, additional chlorofluorohydrocarbon, propane/butane or dimethyl ether may be additionally included as propellants.

When the formulation of the composition is a solution or emulsion, a solvent, solvating agent or emulsifying agent is used as a carrier component. For example, water, ethanol, isopropanol, ethyl carbonate, ethyl acetate, benzyl alcohol, benzyl benzoate, propylene glycol, 1,3-butylglycol oil, glycerol fatty esters, polyethylene glycol or fatty acid esters of sorbitan may be used.

When the formulation of the composition is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tracanth and the like may be used as a carrier component.

When the formulation of the composition is surfactant-containing cleansing, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glyceride, fatty acid diethanolamide, vegetable oil, linolin derivative or ethoxylated glycerol fatty acid ester and the like may be used as carrier components.

According to an exemplary embodiment, the composition comprising the *Chryseobacterium* sp. strain, the lysate of the *Chryseobacterium* sp. strain, the culture of the *Chryseobacterium* sp. strain, or the extract of the lysate or culture may be a food composition.

The food composition may be in a liquid or solid form. For example, the food composition may include various foods, beverages, gum, tea, vitamin complexes, health supplements, etc., and may be used in the form of powder, granule, tablet, capsule or beverage. Each formulation of the food composition can be appropriately selected and formulated by those skilled in the art without difficulty depending on the formulation or purpose of use of ingredients commonly used in the field, and when applied simultaneously with other raw materials, a synergistic effect may occur.

The liquid formulation may include various flavoring agents or natural carbohydrates as additional ingredients like a conventional beverage. Examples of the natural carbohydrate include monosaccharides, disaccharides such as glucose and fructose, polysaccharides such as maltose and sucrose, common sugars such as dextrin and cyclodextrin, and sugar alcohols such as xylitol, sorbitol, and erythritol etc. As the above flavoring agent, natural flavoring agents (taumatin, stevia extract (e.g., rebaudioside A, glycyrrhizin, etc.) and synthetic flavoring agents (e.g., saccharin, aspartame, etc.) can be advantageously used. The proportion of the natural carbohydrate may be generally about 1 to 20 g, in one aspect, about 5 to 12 g per 100 ml of the composition.

In one aspect, the food composition may include various nutrients, vitamins, minerals (electrolytes), flavoring agents such as synthetic flavoring agents and natural flavoring agents, coloring agents and fillers (cheese, chocolate, etc.), pectic acid and a salt thereof, alginic acid and a salt thereof, organic acids, a protective colloidal thickening agent, a pH regulator, a stabilizer, a preservative, glycerin, alcohol, a carbonate used in carbonated beverages, and the like. In another aspect, it may include pulp for the production of natural fruit juices and vegetable beverages. The above components may be used independently or in combination. The proportion of the additive may vary, but is generally selected from 0.001 to about 20 parts by weight based on 100 parts by weight of the composition.

According to an exemplary embodiment, the composition comprising the *Chryseobacterium* sp. strain, the lysate of the *Chryseobacterium* sp. strain, the culture of the *Chryseobacterium* sp. strain, or the extract of the lysate or culture may be a pharmaceutical composition.

The pharmaceutical composition may further include pharmaceutical adjuvants such as preservatives, stabilizers, wetting agents or emulsification accelerators, salts and/or buffers for regulating osmotic pressure, and other therapeutically useful substances, and the pharmaceutical composition can be formulated in various oral or parenteral administration agents according to a conventional method.

The oral administration agents may include, for example, tablets, pills, hard and soft capsules, solutions, suspensions, emulsifiers, syrups, dusts, powders, fine granules, granules, pellets, etc., and these formulations may include surfactants, diluents (e.g., lactose, dextrose, sucrose, mannitol, sorbitol, cellulose and glycine), lubricants (e.g., silica, talc, stearic acid and its magnesium or calcium salts and polyethylene glycol). Tablets may also include binders such as magnesium aluminum silicate, starch paste, gelatin, tragacanth, methylcellulose, sodium carboxymethylcellulose and polyvinylpyrrolidine, optionally pharmaceutical additives such as disintegrants like starch, agar, alginic acid or its sodium salt, absorbents, colorants, flavoring agents, and sweetening agents. The tablet may be prepared by a conventional mixing, granulating or coating method.

In addition, the parenteral administration form may be a transdermal administration, for example, injections, drops, ointments, lotions, gels, creams, sprays, suspensions, emulsions, patches, etc., but is not limited thereto.

The dosage of the active ingredient is determined within the level of those of ordinary skill in the art, and the daily dosage of the drug varies depending on various factors such as the progress of a subject to be administered, onset time, age, health status, complications, etc. On the basis of an adult, 1 μg/kg to 200 mg/kg of the composition in one aspect, and 50 μg/kg to 50 mg/kg in another aspect may be administered in divided doses 1 to 3 times a day.

The pharmaceutical composition may be an external preparation for the skin, and the external preparation for skin is a generic term that may include anything applied outside the skin, and various formulations of pharmaceuticals may be included here.

In an exemplary embodiment, the composition comprising the *Chryseobacterium* sp. strain, the lysate of the *Chryseobacterium* sp. strain, the culture of the *Chryseobacterium* sp. strain, or the extract of the lysate or culture may comprise 0.0001 to 99.99% by weight of the *Chryseobacterium* sp. strain, the lysate of the *Chryseobacterium* sp. strain, the culture of the *Chryseobacterium* sp. strain or the extract of the lysate or culture, based on the total weight of the composition.

In another exemplary embodiment, the composition comprising the *Chryseobacterium* sp. strain, the lysate of the *Chryseobacterium* sp. strain, the culture of the *Chryseobacterium* sp. strain, or the extract of the lysate or culture may comprise 0.0001% by weight or more, 0.001% by weight or more, 0.01% by weight or more, or 0.1% by weight or more, or 20% by weight or less, 15% by weight or less, 10% by weight or less, 5% by weight or less, 1% by weight or less, 0.1% by weight or less, 0.01% by weight or less, or 0.001% by weight or less of the *Chryseobacterium* sp. strain, the lysate of the *Chryseobacterium* sp. strain, the culture of the *Chryseobacterium* sp. strain, or the extract of the lysate or culture, based on the total weight of the composition.

For example, the composition comprising the *Chryseobacterium* sp. strain, the lysate of the *Chryseobacterium* sp. strain, the culture of the *Chryseobacterium* sp. strain, or the extract of the lysate or culture may comprise 0.0001 to 1% by weight, 0.0001 to 0.5% by weight, 0.0001 to 0.1% by weight, 0.0001 to 0.05% by weight, 0.0001 to 0.01% by weight, 0.0001 to 0.005% by weight, 0.0001 to 0.001% by weight, 0.0005 to 0.001% by weight of the *Chryseobacterium* sp. strain, the lysate of the *Chryseobacterium* sp. strain, the culture of the *Chryseobacterium* sp. strain, or the extract of the lysate or culture, based on the total weight of the composition.

MODE FOR INVENTION

Hereinafter, the present disclosure will be described in more detail with examples. These examples are only for illustrating the present disclosure, and it will be apparent to Example 1. Preparation of a Culture of a *Chryseobacterium* sp. Strain In this example, using the *Chryseobacterium Camellia* strain as the *Chryseobacterium* sp. strain, the culture of the *Chryseobacterium* sp. strain was prepared as follows. As the *Chryseobacterium Camellia* strain, the *Chryseobacterium Camellia* Dolsongi-HT1 strain with accession number KCCM11883P, which was deposited at KOREAN CULTURE CENTER OF MICROORGANISMS (KCCM) of Yurim B/D 45 Hongjenae-2ga-gil, Seodaemun-gu, Seoul, 03641 on Sep. 1, 2016 under the provisions of the Budapest Treaty, was used. The strain can be obtained according to the separation and identification method as described in Korean Patent Publication No. 10-2018-0035682. This document is hereby incorporated by reference in its entirety.

(1) Isolation of Microorganisms from Green Tea

In order to select the microorganisms having plant-derived keratin-decomposing activity, a liquid minimal medium using keratin as a carbon and nitrogen source (M9 medium containing 0.5% soluble keratin: $CaCl_2$) 0.015 g/L, $Na_2HPO_4$ 6.78 g/L, $KH_2PO_4$ 3 g/L, NaCl 0.5 g/L, $MgSO_4$ 0.5 g/L) was used to incubate microorganisms at 30° C. or 37° C.

The method for selecting microorganisms using the minimal medium is a method of selecting a target microorganism according to the growth rate of the microorganism. Since microorganisms with low keratinase activity are spontaneously removed in a culturing step, active microorganisms containing highly active enzymes can be selected. It means that microorganisms capable of growing in the minimal medium have keratinase activity.

Accordingly, the microorganisms having keratin-degrading activity were isolated from green tea from Dolsongi tea plantation in Jeju Island, Korea in a limited medium.

(2) Identification of Isolated Microorganisms

In order to identify the isolated microorganisms having keratinase activity, a DNA sequence encoding a partial 16S ribosomal RNA sequence of the microorganisms was analyzed to determine the species and genus name.

After the microorganisms were cultured in a liquid medium, genomic DNA was extracted from the microorganisms, and amplified by a polymerase chain reaction (PCR) using 27F (5'-AGAGTTTGATCMTGGCTCAG-3', SEQ ID NO: 2)/1492R (5'-TACGGYTACCTTGTTACGACTT-3', SEQ ID NO: 3), which is a primer generally used for bacterial identification, and its sequence was analyzed.

As a result of sequencing, it was shown that the sequences had 99% homology with the partial 16S rRNA sequence of *Chryseobacterium camelliae* strain THG C4-1 (KACC 16985; Sequence accession number (16S rRNA) JX843771) and 98% homology with the partial 16S rRNA sequence of *Chryseobacterium taiwanense*.

Accordingly, the novel microbial strain isolated and cultured was confirmed to be *Chryseobacterium camelliae* by the molecular phylogenetic analysis based on the 16S rDNA sequence, and this was named *Chryseobacterium camelliae* Dolsongi-HT1, and this new microbial strain was deposited with accession number KCCM11883P at the Korea Culture Center of Microorganisms (KCCM), a depository institution on Sep. 1, 2016. The partial 16S rDNA sequence of *Chryseobacterium camelliae* Dolsongi-HT1 strain of SEQ ID NO: 1 is shown in FIG. 1.

(3) Preparation of Microbial Cultures

After seed culture of *Chryseobacterium camelliae* Dolsongi-HT1 strain derived from green tea for 15 hours, 10 mL of the cultured strain was inoculated to 1 L of the optimal medium (1% Tryptone/1% NaCl/0.5% Skim milk) and incubated at 30° C. at 200 rpm for 15 hours. After culturing, a culture solution from which microorganisms were removed was obtained, which was concentrated by ultrafiltration (10 KDa) and washed twice with distilled water. Thereafter, it was filtered using a sterile filter (0.2 µm) and then freeze-dried to obtain a concentrated powder of the culture (referred to as HT1).

Example 2. Evaluation of Lipofuscin Accumulation Inhibitory Efficacy after Subculture of Dermal Fibroblasts (1) Culture of Dermal Fibroblast Normal human dermal fibroblasts (NHDF, Lonza Group (LONZA™), Switzerland) from a 59-year-old male were cultured in DMEM medium (Dulbecco's modified Eagle's Medium, Grand Island Biological Company (GIBCO™) 1210-0038) containing 10% fetal bovin serum. All cultures were performed in an incubator at 37° C. and 5% $CO_2$ conditions. Cells having a passage number of 6 to 9 were considered young cells, and it was passaged 20 times while subculturing at the cell number ratio of 1:5.

(2) Sample Processing and Lipofuscin Measurement

The dermal fibroblasts cultured in (1) above were subcultured 20 times while treated with the culture of the *Chryseobacterium* sp. strain obtained in Example 1 at a concentration of 12.5 ppm once every 2 days.

Thereafter, each cell was washed and placed in a 96-well plate, and the autofluorescence of the lipofuscin pigment was measured using a fluorescence plate reader (Synergy H1 Hybrid Multi-Mode Microplate Reader, BioTek Instruments (BIOTEK™). The measurement wavelength was measured under the conditions of excitation 340-410 nm and emission 440-480 nm. In addition, the subcultured cells were observed under a fluorescent microscope (LSM800, Carl Zeiss AG (ZEISS™)).

As a result, as shown in FIGS. 2 and 3, the cells aged 20 passages (indicated as P20 in FIGS. 2 and 3) showed a significantly increased amount of lipofuscin compared to cells passaged twice (indicated as P2 in FIGS. 2 and 3). In the case of the experimental group (indicated as 12.5 ppm in FIGS. 2 and 3) treated with the culture of the *Chryseobacterium* sp. strain together with 20 passages, the amount of lipofuscin was reduced by about 36.4%. Therefore, it was confirmed that the culture of the *Chryseobacterium* sp. strain have the effect of reducing the amount of lipofuscin that is increased or accumulated due to aging.

Example 3. Evaluation of Lipofuscin Elimination Efficacy after Doxorubicin Treatment Cellular senescence was induced by treating keratinocytes and fibroblasts with doxorubicin, known as a substance that induces aging, respectively, and then the lipofuscin elimination efficacy of the *Chryseobacterium* sp. strain culture obtained in Example 1 was evaluated and confirmed as follows.

Normal human keratinocytes (Lonza Group (LONZA™), Switzerland) were cultured using KGM™ Gold Keratinocyte Growth Medium BulletKit. In addition, normal human dermal fibroblasts (Lonza Group (LONZA™), Switzerland) were cultured in DMEM medium (Dulbecco's modified Eagle's Medium, Grand Island Biological Company (GIBCO™) 1210-0038) containing 10% fetal bovin serum. All cultures were performed in an incubator at 37° C. and 5% $CO_2$ conditions. To induce lipofuscin production, 70% confluent keratinocytes and dermal fibroblasts in 4×105 cells/6 well were treated with 100 ng/ml of insulin-like growth factor-1 (IGF1) and 100 nM doxorubicin, respectively, once every two days and cultured for 7 days. Then, the lipofuscin-produced cells were treated with the culture of the *Chryseobacterium* sp. strain obtained in Example 1 at various concentrations of 1.25 ppm, 2.5 ppm, 5 ppm and 10 ppm for 7 days. After fixing the cells in 10% formalin solution for 15 minutes, the fluorescence density was measured using a fluorescent microscope (LSM800, Carl Zeiss AG (ZEISS™)), and the results are shown in FIGS. 4 and 5. The measurement wavelength was measured under the conditions of excitation 400 nm and emission 570 nm.

As a result, when the keratinocytes were treated with IGF1 and doxorubicin, about 80% or more of lipofuscin was produced compared to untreated cells. In the case of the experimental group treated with the culture of *Chryseobacterium* sp. strain after lipofuscin production, lipofuscin was removed in a concentration-dependent manner. In addition, when the fibroblasts were treated with IGF1 and doxorubicin, about 90% or more of lipofuscin was produced compared to untreated cells. In the case of the experimental group treated with the culture of *Chryseobacterium* sp. strain after lipofuscin production, lipofuscin was removed in a concentration-dependent manner. Therefore, it was confirmed that the culture of the *Chryseobacterium* sp. strain have the effect of removing lipofuscin produced due to aging.

Formulation examples of the composition according to one aspect of the present disclosure are described below, but other various formulations may also be applied, which is not intended to limit the present disclosure, but merely to illustrate the present disclosure.

Formulation Example 1. Softening Lotion

A softening lotion was prepared according to a conventional manufacturing method by mixing 0.01% by weight of the culture of the *Chryseobacterium* sp. strain of Example 1, 3% by weight of glycerin, 2% by weight of butylene glycol, 2% by weight of propylene glycol, 0.1% by weight of carboxyvinyl polymer, 10% by weight of ethanol, 0.1% by weight of triethanolamine, a trace amount of preservative, a trace amount of colorant, a trace amount of fragrance, and a balance of purified water.

Formulation Example 2. Nutrient Lotion

A nutrient lotion was prepared according to a conventional manufacturing method by mixing 0.01% by weight of the culture of the *Chryseobacterium* sp. strain of Example 1, 4% by weight of beeswax, 1.5% by weight of polysorbate 60, 0.5% by weight of sorbitan sesquioleate, 5% by weight of liquid paraffin, 5% by weight of squalane, 5% by weight of caprylic/capric triglyceride, 3% by weight of glycerin, 3% by weight of butylene glycol, 3% by weight of propylene glycol, 0.1% by weight of carboxyvinyl polymer, 0.2% by weight of triethanolamine, a trace amount of preservative, a trace amount of colorant, a trace amount of fragrance and a balance of purified water.

Formulation Example 3. Nourishing Cream

A nutritional cream was prepared according to a conventional manufacturing method by mixing 0.01% by weight of the culture of the *Chryseobacterium* sp. strain of Example 1, 10% by weight of beeswax, 1.5% by weight of polysorbate 60, 0.5% by weight of sorbitan sesquioleate, 10% by weight of liquid paraffin, 5% by weight of squalane, 5% by weight of caprylic/capric triglyceride, 5% by weight of glycerin, 3% by weight of butylene glycol, 3% by weight of propylene glycol, 0.2% by weight of triethanolamine, a trace amount of preservative, a trace amount of colorant, a trace amount of fragrance and a balance of purified water.

Formulation Example 4. Pack

A pack was prepared according to a conventional manufacturing method by mixing 0.01% by weight of the culture of the *Chryseobacterium* sp. strain of Example 1, 13% by weight of polyvinyl alcohol, 0.2% by weight of sodium carboxymethylcellulose, 0.1% by weight of allantoin, 5% by weight of ethanol, 0.3% by weight of nonylphenyl ether, a trace amount of preservative, a trace amount of colorant, a trace amount of fragrance, and a balance of purified water.

Formulation Example 5. Drug for Topical Administration (Patch Agent)

According to the composition shown in Table 1 below, a drug for topical administration (patch agent) was prepared in a conventional manner.

TABLE 1

| Name of raw material | content(wt %) |
|---|---|
| Culture of *Chryseobacterium* sp. strain of Example 1 | 2.0 |
| beta-1,3-glucan | 3.0 |
| diethylamine | 0.7 |
| sodium sulfite | 0.1 |
| polyoxyethylene lauryl ether (E.O = 9) | 1.0 |
| polyhydroxyethylene cetyl stearyl ether (Cetomacrogol 1000) | 1.0 |
| viscous paraffin oil | 2.5 |
| caprylic acid ester/capric acid ester (Cetiol LC) | 2.5 |
| polyethylene glycol 400 | 3.0 |
| polyacrylic acid (Carbopol 934P) | 1.0 |
| Purified water | balance |
| total | 100 |

Formulation Example 6. Powder

A powder was prepared by mixing 2 g of the culture of the *Chryseobacterium* sp. strain of Example 1 and 1 g of lactose, and then filling the mixture in an airtight bag.

Formulation Example 7. Tablet

A tablet was prepared by mixing 100 mg of the culture of the *Chryseobacterium* sp. strain of Example 1, 100 mg of corn starch, 100 mg of lactose, and 2 mg of magnesium stearate, and tableting the mixture according to a conventional manufacturing method.

Formulation Example 8. Capsule

A capsule was manufactured by mixing 100 mg of the culture of the *Chryseobacterium* sp. strain of Example 1, 100 mg of corn starch, 100 mg of lactose, and 2 mg of magnesium stearate, and filling the mixture in a gelatin capsule according to a conventional manufacturing method.

Formulation Example 9. Pill

A pill was prepared by mixing the culture of the *Chryseobacterium* sp. strain of Example 1, 1.5 g of lactose, 1 g of glycerin, and 0.5 g of xylitol, and processing the mixture so as to be 4 g per pill according to a conventional manufacturing method.

Formulation Example 10. Granule

Granules were prepared by mixing 150 g of the culture of the *Chryseobacterium* sp. strain of Example 1, 50 mg of soybean extract, 200 mg of glucose, and 600 mg of starch, adding 100 mg of 30% ethanol to the mixture to dry the mixture at 60° C., and filling the mixture in a bag.

Formulation Example 11. Drinks 50 mg of the culture of the *Chryseobacterium* sp. strain of Example 1, 10 g of glucose, 0.6 g of citric acid, and 25 g of liquid oligosaccharide were mixed, 300 ml of purified water was added to the mixture, and 200 ml of the mixture was filled into each bottle. After filling the bottle, it was sterilized at 130° C. for 4 to 5 seconds to prepare drinks.

Formulation Example 12. Caramel

Caramel was prepared by mixing 50 mg of the culture of the *Chryseobacterium* sp. strain of Example 1, 1.8 g of corn syrup, 0.5 g of skim milk, 0.5 g of soybean lecithin, 0.6 g of butter, 0.4 g of hydrogenated vegetable oil, 1.4 g of sugar, 0.58 g of margarine, and 20 mg of salt and molding the mixture.

Specific parts of the present disclosure have been described in detail above. It will be apparent to those of ordinary skill in the art that these specific descriptions are merely preferred embodiments, and the scope of the present disclosure is not limited thereby. Accordingly, the substantial scope of the present disclosure is defined by the appended claims and their equivalents.

[Accession Number]
Name of depository institution: Korea Culture Center of Microorganisms
Accession Number: KCCM11883P
Deposit Date: 2016 Sep. 1

---

The invention claimed is:

1. A method for inhibiting lipofuscin accumulation or removing lipofuscin, comprising administering to a subject in need thereof a composition comprising a *Chryseobacterium* sp. strain, a lysate of the *Chryseobacterium* sp. strain, a culture of the *Chryseobacterium* sp. strain, or an extract of the lysate or culture in an effective amount, wherein the strain is a *Chryseobacterium camelliae* Dolsongi-HT1 strain with accession number of KCCM11883P.

2. The method according to claim 1, wherein the composition comprises the culture of the *Chryseobacterium* sp. strain, or the extract of the culture in an effective amount.

3. The method according to claim 1, wherein the method has an anti-aging effect on the subject.

4. The method according to claim 1, wherein the method lightens the skin color of the subject.

5. The method according to claim 1, wherein the method ameliorates or treats a disease caused by lipofuscin accumulation.

6. The method according to claim 5, wherein the disease caused by the lipofuscin accumulation is one or more selected from the group consisting of sarcopenia, progeria, Alzheimer's disease, Parkinson's disease, amyotrophic lateral sclerosis (ALS), myocardial infarction, age-related macular degeneration, neuronal ceroid lipofuscinoses (NCL), acromegaly, denervation atrophy and chronic obstructive pulmonary disease (COPD).

7. The method according to claim 1, wherein the composition is a cosmetic composition, a food composition, or a pharmaceutical composition.

8. The method according to claim 1, wherein the composition comprises 0.0001 to 99.99% by weight of the *Chryseobacterium* sp. strain, the lysate of the *Chryseobacterium* sp. strain, the culture of the *Chryseobacterium* sp. strain, or the extract of the lysate or culture, based on a total weight of the composition.

* * * * *

SEQUENCE LISTING

```
<160> NUMBER OF SEQ ID NOS: 3

<210> SEQ ID NO 1
<211> LENGTH: 1198
<212> TYPE: DNA
<213> ORGANISM: Unknown
<220> FEATURE:
<223> OTHER INFORMATION: Chryseobacterium camelliae Dolsongi-HT1

<400> SEQUENCE: 1
agctagggtg ggtacggatt attgggttta agggtccgta ggcggatgtg taagtcagtg      60
gtgaaatctc acagcttaac tgtgaaactg ccattgatac tgcatgtctt gagtaaggta     120
gaagtggctg gaataagtag tgtagcggtg aaatgcatag atattactta gaacaccaat     180
tgcgaaggca ggtcactatg tcttaactga cgctgatgga cgaaagcgtg gggagcgaac     240
aggattagat accctggtag tccacgccgt aaacgatgct aactcgtttt tgggttttcg     300
gattcagaga ctaagcgaaa gtgataagtt agccacctgg ggagtacgtt cgcaagaatg     360
aaactcaaag gaattgacgg gggcccgcac aagcggtgga ttatgtggtt taattcgatg     420
atacgcgagg aaccttacca aggcttaaat gggaattgat cggtttagaa atagaccttc     480
cttcgggcaa ttttcaaggt gctgcatggt tgtcgtcagc tcgtgccgtg aggtgttagg     540
ttaagtcctg caacgagcgc aaccctgtt  actagttgct accattaagt tgaggactct     600
agtaagactg cctacgcaag tagagaggaa ggtggggatg acgtcaaatc atcacggccc     660
ttacgccttg ggcacacac  gtaatacaat ggcaggtaca gagggcagct acacagcgat     720
gtgatgcgaa tctcgaaagc ctgtctcagt tcggattgga gtctgcaact cgactctatg     780
aagctggaat cgctagtaat cgcgcatcag ccatggcgcg gtgaatacgt tcccgggcct     840
tgtacacacc gcccgtcaag ccatggaagt ctggggtacc tgaagtcggt gaccgtaaaa     900
ggagctgcct agggtaaaac aggtaactag ggctaatcgt acagggggaaa ccctaaaagt     960 ttaaccagga accggtagaa ggtgttaagg atagagtgta tatctgtttt gtatatgttg    1020
tatttatcta gtgtatctga gataatggat agataacgct cgaactggca ctacactagt    1080
gagagatatt agtattctta tatattaagt ctctattgag atatcataat cgtggataaa    1140
```

```
gacttgacag cggcgagagc ctggatagcg gagtggtgtt agctatgagt gtataatc      1198

<210> SEQ ID NO 2
<211> LENGTH: 20
<212> TYPE: DNA
<213> ORGANISM: Artificial Sequence
<220> FEATURE:
<223> OTHER INFORMATION: 27F primer

<400> SEQUENCE: 2
agagtttgat cmtggctcag                                                  20

<210> SEQ ID NO 3
<211> LENGTH: 22
<212> TYPE: DNA
<213> ORGANISM: Artificial Sequence
<220> FEATURE:
<223> OTHER INFORMATION: 1492R primer

<400> SEQUENCE: 3
tacggytacc ttgttacgac tt                                               22
```